US012434017B2

(12) United States Patent
Orphanos et al.

(10) Patent No.: US 12,434,017 B2
(45) Date of Patent: Oct. 7, 2025

(54) SURGICAL INSUFFLATION SYSTEMS AND METHODS FOR USE

(71) Applicant: Saphena Medical, Inc., West Bridgewater, MA (US)

(72) Inventors: Mark J. Orphanos, Foxboro, MA (US); Michael Glennon, Norwell, MA (US)

(73) Assignee: Saphena Medical, Inc., West Bridgewater, MA (US)

(*) Notice: Subject to any disclaimer, the term of this patent is extended or adjusted under 35 U.S.C. 154(b) by 205 days.

(21) Appl. No.: 16/862,947

(22) Filed: Apr. 30, 2020

(65) Prior Publication Data

US 2020/0345954 A1 Nov. 5, 2020

Related U.S. Application Data

(60) Provisional application No. 62/841,409, filed on May 1, 2019.

(51) Int. Cl.
*A61M 13/00* (2006.01)

(52) U.S. Cl.
CPC ... *A61M 13/003* (2013.01); *A61M 2202/0225* (2013.01)

(58) Field of Classification Search
CPC ................ A61M 13/00; A61M 13/003; A61M 2202/0225; A61B 17/3205; A61B 17/3203; A61B 2017/00548
USPC .......................................................... 606/190
See application file for complete search history.

(56) References Cited

U.S. PATENT DOCUMENTS 4,357,940 A * 11/1982 Muller .................. A61B 90/00 606/190
5,399,159 A 3/1995 Chin et al.
5,419,772 A * 5/1995 Teitz .................. A61M 3/0233 604/249
5,454,791 A 10/1995 Tovey et al.
5,587,736 A 12/1996 Walls
(Continued)

FOREIGN PATENT DOCUMENTS

DE 202019100208 U1 1/2019
JP 2004008241 A 1/2004
JP 2011056276 A 3/2011

OTHER PUBLICATIONS

International Search Report issued in corresponding International Patent Application No. PCT/US2020/030665, mailed Jul. 16, 2020 (2 pages).

(Continued)

*Primary Examiner* — Laura A Bouchelle
*Assistant Examiner* — Anna E Goldberg-Richmeier
(74) *Attorney, Agent, or Firm* — SCHWEGMAN LUNDBERG & WOESSNER, P.A.

(57) ABSTRACT

The present invention provides systems, methods and devices for delivering media. The device can include a body designed to accommodate at least one cannister of a media, an body coupled to the body and having a distal end, and a tapered tip disposed at the distal end of the body and in fluid communication with the cannister, the tip being designed for advancing the distal end to a site of interest and through which media from the cannister can be directed to the site of interest. The device can also include a dispersion mechanism coupled to the body for controlled release of the media out the tapered tip.

20 Claims, 9 Drawing Sheets

(56) References Cited

U.S. PATENT DOCUMENTS

| | | | | |
|---|---|---|---|---|
| 5,630,783 | A * | 5/1997 | Steinberg | A61B 1/015 600/179 |
| 9,119,900 | B2 | 9/2015 | Chin | |
| 9,283,045 | B2 | 3/2016 | Rhee et al. | |
| 9,498,246 | B2 | 11/2016 | Chin et al. | |
| 9,814,481 | B2 | 11/2017 | Orphanos et al. | |
| 9,943,328 | B2 | 4/2018 | Orphanos et al. | |
| 2003/0032916 | A1 | 2/2003 | Rowe et al. | |
| 2003/0181917 | A1 | 9/2003 | Gertner | |
| 2004/0133228 | A1 | 7/2004 | Bayer | |
| 2005/0065511 | A1 | 3/2005 | Geistert | |
| 2005/0159764 | A1 * | 7/2005 | Kasahara | A61B 17/00008 606/159 |
| 2005/0171528 | A1 * | 8/2005 | Sartor | A61B 18/042 606/41 |
| 2010/0292533 | A1 * | 11/2010 | Kasahara | A61B 1/012 600/104 |
| 2013/0197299 | A1 * | 8/2013 | Chin | A61F 2/062 600/36 |
| 2015/0133924 | A1 | 5/2015 | McLawhorn et al. | |
| 2017/0332884 | A1 | 11/2017 | Amling et al. | |
| 2018/0042694 | A1 | 2/2018 | Kadykowski | |
| 2019/0192188 | A1 | 6/2019 | Orphanos et al. | |

OTHER PUBLICATIONS

International Search Report and Written Opinion in International Application PCT/US2019/051953 mailed Nov. 19, 2019 (14 pages).

* cited by examiner

SURGICAL INSUFFLATION SYSTEMS AND METHODS FOR USE

CROSS-REFERENCE TO RELATED APPLICATION(S)

This application claims priority to, and the benefit of, U.S. Provisional Application No. 62/841,409, filed May 1, 2019, for all subject matter common to both applications. The disclosure of said provisional application is hereby incorporated by reference in its entirety.

TECHNICAL FIELD

The presently disclosed embodiments relate to surgical insufflation systems, and more particularly, to a device for introducing gas insufflation and irrigation for vessel harvesting systems and methods of their use.

BACKGROUND

Vessel harvesting is a surgical technique that is commonly used in conjunction with coronary artery bypass surgery. During a bypass surgery, blood may be rerouted to bypass blocked arteries to restore and improve blood flow and oxygen to the heart. In some instances, the blood may be rerouted using a bypass graft, where one end of the by-pass graft is attached to a blood source upstream of the blocked area and the other end is attached downstream of the blocked area, creating a "conduit" channel or new blood flow connection bypassing the blocked area. Commonly, a surgeon will remove or "harvest" healthy blood vessels from another part of the body to create the bypass graft. The success of coronary artery bypass graft surgery may be influenced by the quality of the conduit and how it is handled or treated during the vessel harvest and preparation steps prior to grafting.

Vessel harvesting methods involve selecting a vessel, traditionally, the great saphenous vein in the leg or the radial artery in the arm to be used as a bypass conduit sealing off and cutting smaller blood vessels that branch off the main vessel conduit and harvesting the main conduit from the body. This practice does not harm the remaining blood vessel network, which heals and maintains sufficient blood flow to the extremities, allowing the patient to return to normal function without noticeable effects.

A minimally invasive technique for vessel harvesting is known as endoscopic vessel harvesting ("EVH"), a procedure that requires only small incisions. During EVH and similar surgical procedures, media can be insufflated or injected into the patient's leg cavity to expand the leg cavity and provide a good visual field inside the leg cavity (or other area) or flush tissue or components. Traditionally, the insufflation media is provided in the operating room ("OR") and delivered via a flexible tube couple to a medical device located within the sterile field.

Some EVH devices have small lengths of tubing extending from their bodies at the handle with which the operator (e.g., surgeon, physician assistant) can connect an OR tube. In some instances, the connection can be included on the flexible trocar of the EVH device. Conventionally, trocars can be inserted into a surgical site of a patient to serve as a portal for subsequent introduction of insufflation gas and/or placement of other instruments into the surgical site. However, conventional trocars are large, awkward, can be difficult to accurately insert and place within the patient. Additionally, the trocar and the OR tube must be present in the sterile field and is attached to the EVH system at or near the handle of the device, where the operator's hands are, atop the OR table.

In current methods, the hospital OR provides a source of $CO_2$, which is normally a very large cylinder of gas attached to a rolling cart and an insufflator machine. The insufflator machine receives input gas from the storage tanks and releases it out an insufflation tube at a user-defined flowrate and pressure setting. On the end of that insufflation tube is a male luer connector. A device such as an EVH device can be designed to attach to this insufflation tube (e.g., via a female luer on the device), which mates to the OR tube and receives the output flow from the insufflation machine to be delivered to the patient. Throughout the procedure, the insufflation machine will adjust the flowrate (up to a user defined maximum) in order to achieve the desired pressure setting (also set by the user in advance).

The foregoing arrangement for performing an EVH procedure in a typical OR setting is illustrated in FIG. 1. As provided in FIG. 1, there are many tubes, wires, and instruments that clutter the OR table and the sterile field, thereby impeding the progress of the operator (e.g., surgeon, physician assistant) and increasing the chance or error, infection, etc. caused by the additional tubes, wires, etc. Frequently the tubing and wires become entangled as the EVH device is rotated during a normal EVH procedure. It is therefore advantageous to remove as many tubes and wires as possible from this area, to minimize the clutter in the sterile field and simplify the EVH procedure. Such OR table and sterile field cluttering and the resulting entanglement and related difficulties are also present in other types of laparoscopic and endoscopic surgical procedures.

SUMMARY

The present disclosure provides systems and methods for providing insufflation media (i.e., fluids such as gases (e.g., $CO_2$) or liquids (e.g., saline)) during a surgical procedure that minimize clutter in the sterile field and on the OR table, to ultimately simplify the procedure.

In accordance with example embodiments of the present invention, a surgical device is provided. The surgical device includes a body designed to accommodate at least one canister of a media, the body having a distal end, and a tapered tip disposed at the distal end of the body and in fluid communication with the canister, the tip being designed for advancing the distal end to a site of interest and through which media from the canister can be directed to the site of interest. The device also includes a dispersion mechanism coupled to the body for controlled release of the media out the tapered tip.

In accordance with aspects of the present invention, the surgical device further includes a canister connection point coupling the canister of the media to the body. The surgical device can further include a conduit within the body for delivering the media from the canister to the tip. The surgical device can be an endoscopic vessel harvesting device. The conduit can be an insufflation conduit. The conduit can be an irrigation conduit. The canister can be a pressurized canister. The canister can be a pressurized from approximately 800 psi to 1200 psi. The media in the canister can be an insufflation fluid or an irrigation fluid. The media in the canister can be $CO_2$.

In accordance with example embodiments of the present invention, a method for delivering media is provided. The method includes providing a surgical device having a tapered tip at a distal end of the device, at least one canister of media in fluid communication with the tapered tip, and a dispersion mechanism for controlled release of the media through the surgical device and out of the tapered tip, directing the tapered tip to a site of interest, and delivering the media from canister out the tapered tip to the site of interest in a controlled manner.

In accordance with aspects of the present invention, the method is performed during an endoscopic vessel harvesting procedure. The media delivering step can include insufflating the patient's body part. The media delivering step can include irrigating the patient's body part. The method can further include placing a sealing device at an incision site on the patient's body part to create a gas seal. The step of placing can further include adhering, by an adhesive disposed over at least a portion of a surface of the sealing device the incision site. The method can further include advancing a tip of the surgical instrument to a target anatomical structure.

BRIEF DESCRIPTION OF THE DRAWINGS

Illustrative, non-limiting example embodiments will be more clearly understood from the following detailed description taken in conjunction with the accompanying drawings.

DETAILED DESCRIPTION OF THE EMBODIMENTS

Figure 1:
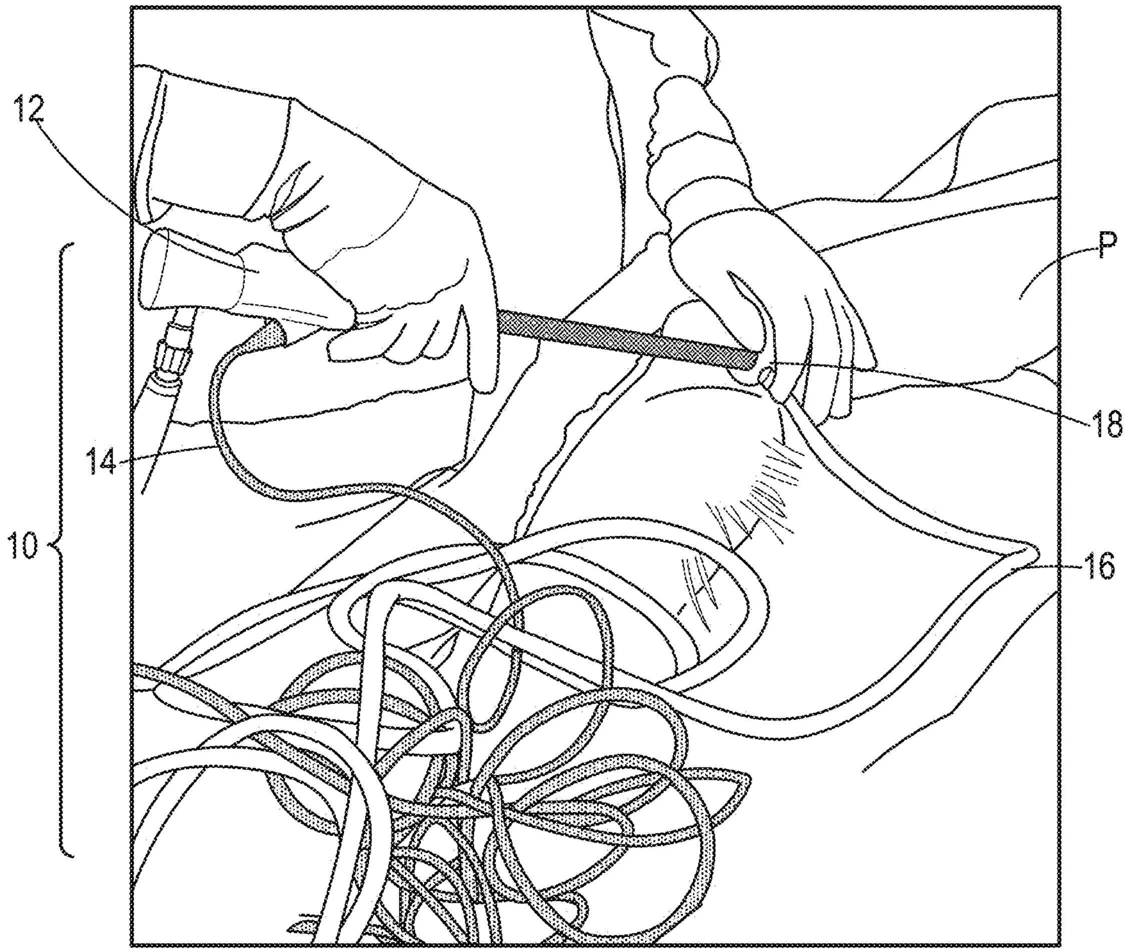
FIG. 1 is an exemplary view of a traditional EVH system.

Various exemplary embodiments will be described more fully hereinafter with reference to the accompanying drawings, in which some example embodiments are shown. The present inventive concept may, however, be embodied in many different forms and should not be construed as limited to the example embodiments set forth herein. Rather, these example embodiments are provided so that this disclosure will be thorough and complete, and will fully convey the scope of the present inventive concept to those skilled in the art. In the drawings, the sizes and relative sizes of layers and regions may be exaggerated for clarity. Like numerals refer to like elements throughout.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Embodiments of the present disclosure generally apply to surgical instruments, such as an endoscopic vessel harvesting (EVH) device. The various embodiments of the present disclosure can be used, for example, to provide a flexible, insufflation device for obviating the need for a trocar, additional OR tubing, and/or other mechanism for connecting a separate fluid or gas introduction system to the surgical instrument. However, the present invention can be utilized for any combination of devices that are designed to delivery of fluid or gases.

The design of the present invention eliminates the need for large OR-provided gas tanks, insufflator machines, and insufflator tubes. Instead, the present invention provides an EVH device that includes or is otherwise directly coupled to one or more canister(s) of highly pressurized CO2 gas without the need for hoses, pumps, etc. The canister(s) can be contained within or otherwise coupled to the body of the EVH device. The canister(s) can be one-time use canister(s) that contain a pre-determined and limited volume of gas. With one-time use canister(s), the EVH device can be disposable and/or be able to receive new canister(s). Administration of the contents of the canister(s) can be controlled by the canister itself or by a mechanism inside the handle of the EVH device, which would control the pressure and flow rate of the gas coming from the canister and being delivered to the patient. The pressure and flow rate could be preset with a pre-determined pressure and/or adjustable through an adjustment mechanism.

Referring to FIG. 1, which illustrates an operator using an existing EVH system 10 during a vessel harvesting procedure on a patient's leg P. The EVH system 10 includes an EVH device 12 having a power cable 14. The EVH system 10 also includes multiple other tubes and wires, including a tube 16 that terminates/forms a connection at a trocar portion 18 of the EVH device 12. The tube 16 can be a media delivery tube provided by the OR. For example, the tube 16 provides insufflation media to trocar portion 18 for use during a procedure. The tube 16 can also provide a media connection formed at an insufflation generator, 5-10 feet away (not shown) instead of at the trocar portion 18, as shown in FIG. 1. Regardless of connections, the media delivery tube 16 is thereby present within the sterile field, creating clutter in the sterile field and on the OR table, and adding complexity to the EVH procedure.

Figure 2A:
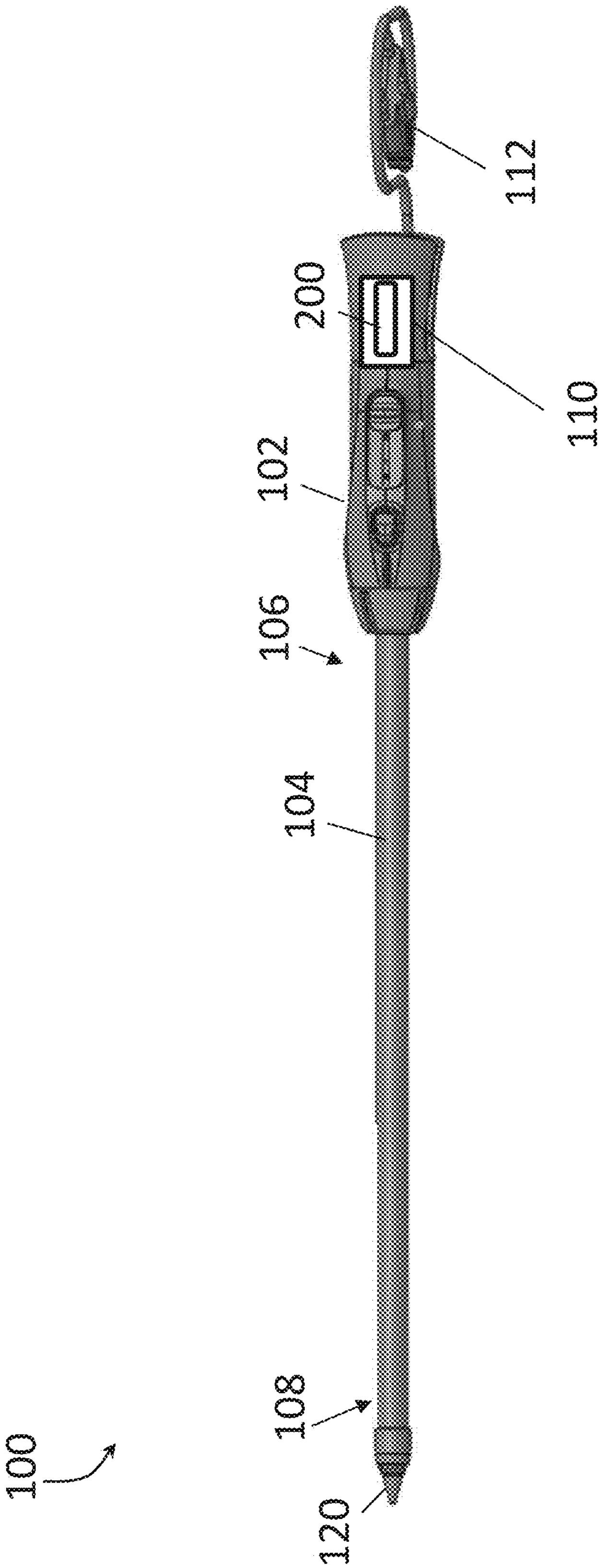
FIG. 2A is an exemplary illustrative side view of a EVH system in accordance with various embodiments.
Figure 2B:
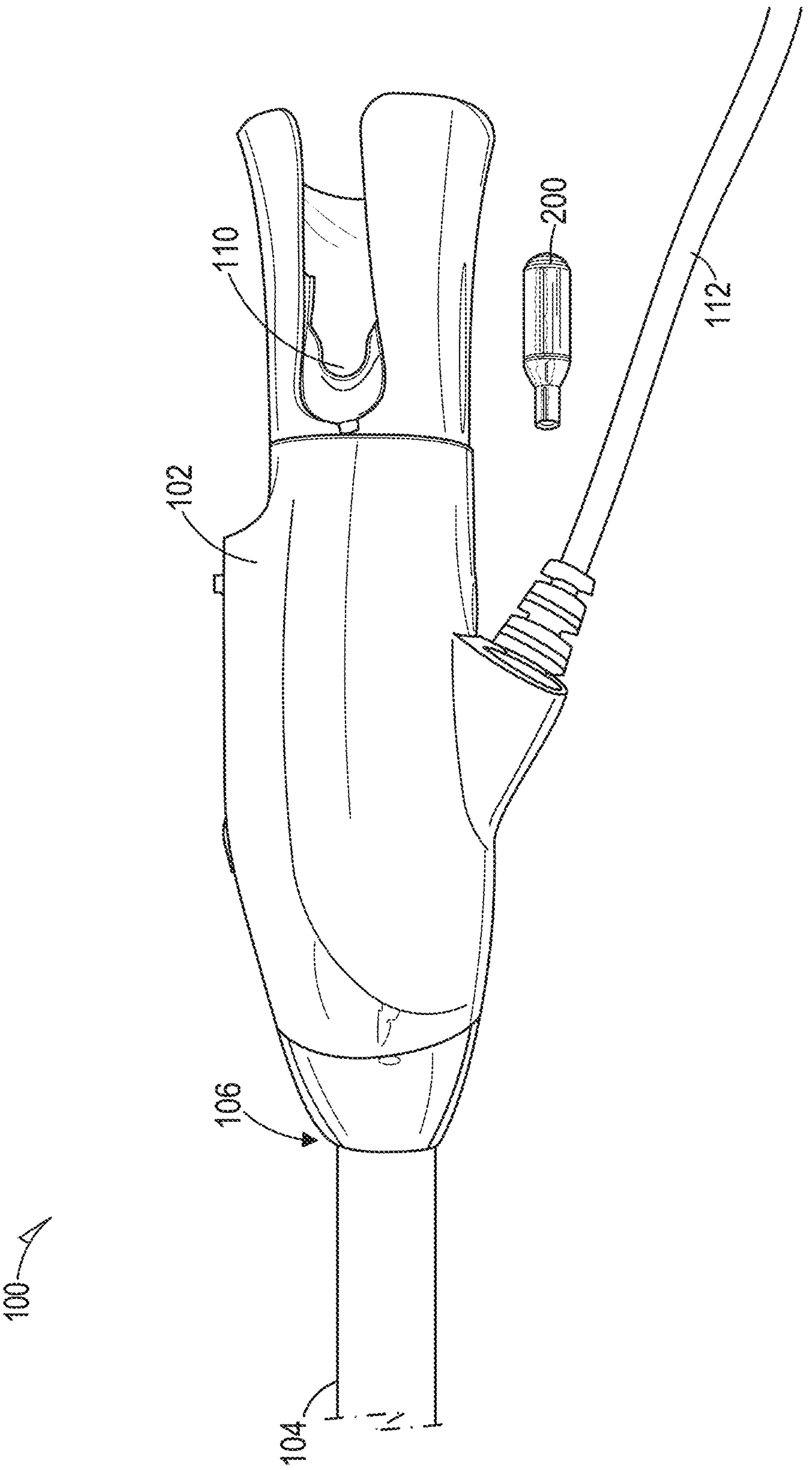
FIG. 2B is an exemplary side view of a EVH system in accordance with various embodiments.
Figure 2C:
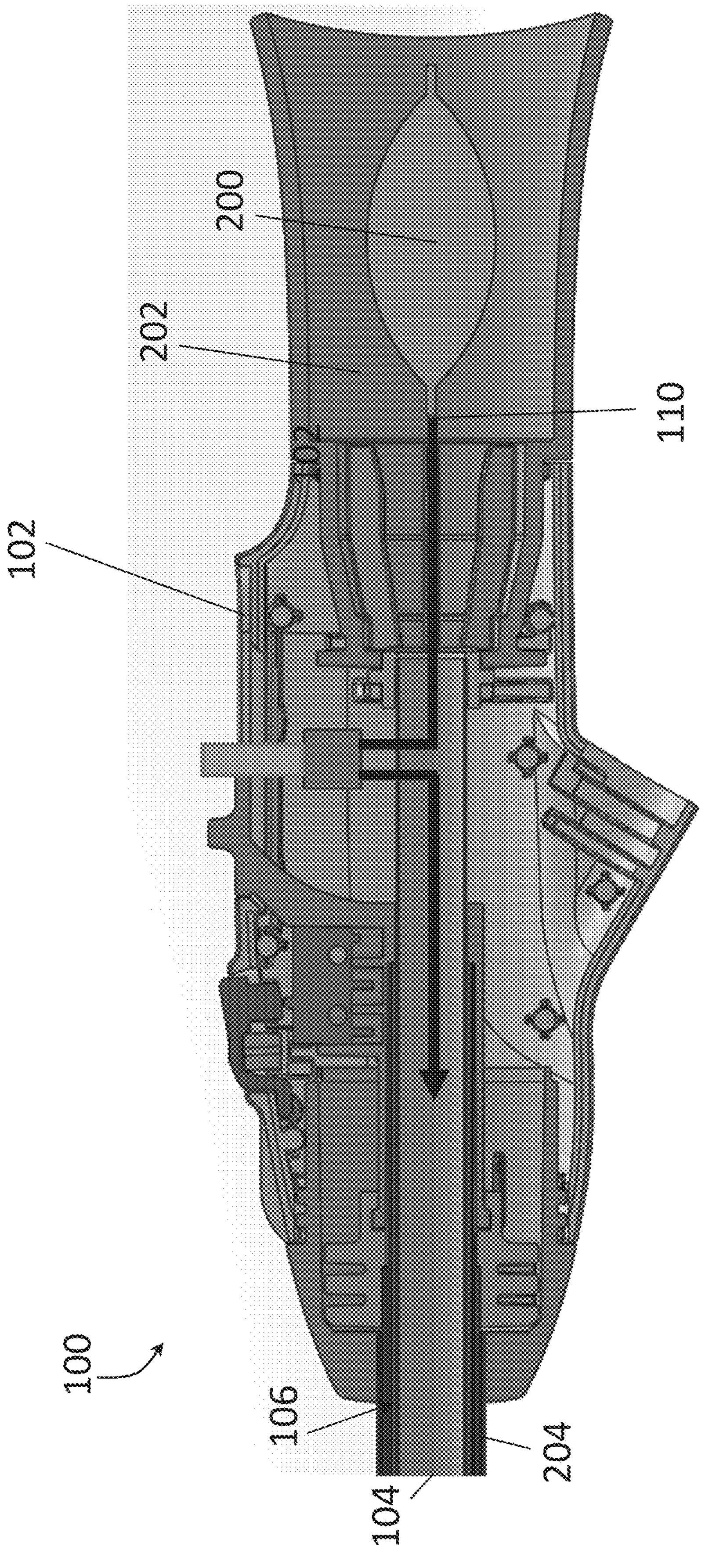
FIG. 2C is an exemplary cross-sectional side view of a EVH system in accordance with various embodiments.

Referring to FIGS. 2A-2C, an exemplary vessel harvesting device 100 in accordance with the present invention is depicted. Referring to FIG. 2A, in some embodiments, the device 100 can include a body having a housing 102 and an elongate body 104 which can be configured to house the various components of the device 100. The housing 102 can include internal wiring to receive and deliver power to said components, and communicate data to systems outside of the housing 102. The housing 102 can also include buttons, switches, etc. for controlling operation of the device 100. For example, the housing 102 can include a button for powering a cutting component of the device 100. The housing 102 can be constructed from any combination of materials utilizing any combination of systems and methods known in the art. For example, the housing 102 can be constructed from a biocompatible material, such as, plastic material, elastomeric material, metallic material, shape memory material, composite material or any other materials that has the desired characteristics. In some embodiments, the device 100 and components thereof can be disposable.

In some embodiments, the housing 102 may be coupled to external wires or cabling 112 that is configured for providing power and transferring data with the device 100 and the subsystems thereof. As would be appreciated by one skilled in the art, the cable 112 can also be configured to provide power to other systems known in the art, for example, a cutting sub-system of the device 100, such as the cutting systems discussed with respect to U.S. Pat. Nos. 9,119,900, 9,498,246, 9,814,481, and 9,943,328 and, all incorporated herein by reference. The cable 112 can provide a combination of wiring for different power and data cabling within a singular shield or can be a combination of wires braided together into a single line. In some embodiments, the device 100 can also include a wireless power source in place of the cable 112. For example, the device 100 can be battery operated.

In some embodiments, the housing 102 can include a canister connection point 110 for receiving and/or coupling the device 100 to one or more fluid/gas media canister(s) 200. Referring to FIG. 2B, the canisters 200 can include any combination of containers constructed from any combination of materials containing releasable fluids (e.g., gases, liquids, etc.). For example, the canisters 200 can be metallic (e.g., aluminum), plastic, an alloy, etc., or a combination thereof based material with pressurized CO2 therein. The canister can be constructed from any combination of materials that provide sufficient strength to withstand the pressure of the media included therein.

Similarly, the canister connection point 110 can have any combination of connection points to receive a canister 200 and withstand a connection with the 200 when pressure is released. For example, the canister connection point 110 can include a threaded coupler, a friction fit connector, a mechanical coupler, etc. As would be appreciated by one skilled in the art, the canister connection point 110 can be configured to receive any combination of canisters 200 and media types with any combination of connection points. For example, the canister connection point 110 can be configured to receive CO2 canisters 200 configured for use during a procedure (e.g., a vessel harvesting procedure). In another example, the cannister may be similar to the canister 200 that cyclists use for inflating the tires on their bikes.

Referring to FIG. 2C, in some embodiments, the canister connection point 110 can include a cavity 202 or can be positioned within a cavity 202 included within the internal structure of the housing 102. The cavity 202 can be sized and shaped such that it can receive and hold one or more canisters 200 as part of the housing 102. The cavity 202 can also be sized and dimensioned to both receive the canisters 200 and couple/secure the canisters with the canister connection point 110. For example, the cavity 202 can provide sufficient space to rotate, clip, push, etc. the canisters 200 into a secure position. The canister connection point 110 and/or cavity 202 can be located at any position on the device 100. For example, the canister connection point 110 can be part of the handle 102, coupled to the elongate body 104 section or any other location on the device 100.

In some embodiments, the canisters 200 can be fixedly attached to the canister connection point 110 for one time use or they can be removably attached to the canister connection point 110 for replacement and reuse. For example, the canister(s) 200 can be placed within the cavity 202 and connected at the canister connection point 110 at the time of manufacture or canister(s) 200 can be accessible by a user (e.g., via a hatch, door, etc.) for insertion and/or removal of the canister(s) 200.

In some embodiments, the canister connection point 110 and/or the cavity 202 can include mechanical components to hold the canisters 200 in place. For example, the canister connection point 110 and/or the cavity 202 can include clips, springs, straps, etc. to hold the canisters 200 securely in place. In some embodiments, the canister connection point 110 can be positioned such that the canister(s) 200 are partially included within the housing 102 of the device 100 and at least partially extend outside of the housing 102. For example, the media release elements and transmission mechanisms can be located internally within the housing 102 while coupling mechanisms can extend externally from the housing 102 to receive and/or couple to canister(s) residing at least partially outside of the housing 102.

Regardless of configuration, the canister connection point 110 can include a coupling mechanism configured to fixedly or removably receive a canister 200 input to securely couple to and create an air-tight seal with the canister(s) 200. For example, the coupling mechanism can be a sealable threaded junction, a sealable click in place junction, a sealable twist in place junction, a friction fitted connection, etc., or a combination thereof There can be additional components to assist in creating a sealed connection, such as a gasket, an O-ring, etc. The canister connection point 110 can be configured to receive any combination of canister types, sizes, and containing any combination of medias at any combination of pressures. For example, the canister connection point 110 can receive canisters 200 containing gas with pressures ranging from 800 psi to 1200 psi with as much volume as possible to provide the desired delivery. Additionally, the pressure and media type on the inside canister 200 can dictate the available volume of media at the pressure desired, for example, a gas at 10-15 mmHg with temperature at or near body temperature. The gas at this temperature and pressure will have a certain density.

Continuing with FIG. 2C, in some embodiments, the canister connection point 110 can be coupled to the elongate body 104 using any combination of structures designed to handle any combination of pressures and medias applied by the canisters 200. For example, the canister connection point 110 can be sized and shaped to receive, transfer, and/or dispense pressurized fluid (e.g., gas or liquid) from an attached canister 200 and into the elongate body 104. Similarly, the canister connection point 110 can be constructed from any combination of materials designed to withstand said pressure and said media. Depending on the location of the canisters 200, the canister connection point 110 can include any combination of mechanisms (e.g., a lumen) designed to deliver media from the attached canisters 200 to the elongate body 104. In some embodiments, the elongate body 104 can include a channel 204 for delivering the media from the canisters 200 and canister connection point 110 through the elongate body 104. The channel 204 can include any combination of spaces, lumens, conduits, discussed herein to provide the media from the canister 200 and dispensed out of the device 100, for example, out of the tip 120.

In some embodiments, the canister connection point 110 can include or otherwise be attached to media release elements, transmission mechanisms, release/dispersion mechanism, etc. The dispersion mechanism can be designed to trigger release of the media (e.g., fluid, gas, liquid, etc.) from any connected canisters 200 to the outside of the EVH device 100 in a controlled manner. For example, the dispersion mechanism can be designed to release media from the canisters 200, transport the released fluid through the elongate body 104 of the device 100, and out the distal end 108 (or other section) of the device 100. The fluid can travel through the elongate body 104 using any combination of structures. For example, the elongate body 104 can include one or more lumens for receiving fluid from the canister 200 (e.g., via the canister connection point 110). In another example, the fluid can be received in a space(s) between components situated within the elongate body 104. The lumens can be any combination of materials, sized, and shapes, for example, the lumens can be flexible or rigid, plastic or metal. In instances when multiple canisters 200 are available, the dispersion mechanism can be designed to release fluid from the canisters 200 individually, simultaneously, subsequently, etc.

In some embodiments, the dispersion mechanism can be or otherwise include a valve to control when and how media is released from the canisters 200. The valve can include any combination of electrical and mechanical valve systems designed to release media from a canister 200. In some embodiments, the valve can include or otherwise be connected to sensors that read pressure in other locations of the device 100. For example, the valve can include sensors at the canister connection point 110 and at the tip 120 to monitor pressures at different points during operation of the device 100. In some embodiments, the dispersion mechanism can include or otherwise be connected to one or more pressure regulators to make sure the body of the device 100 does not receive a pressure above a predetermined threshold. In some embodiments, the dispersion mechanism can include or otherwise be connected to backflow preventers to make sure media travels in one direction, for example, toward the distal end of the device 100 and out the tip 120 or other output location on the device 100.

In some embodiments, the dispersion mechanism can be configured to release the contents of the canisters 200 at a predetermined control rate and/or over a predetermined period of time and/or can be adjustable to vary the rate/pressure of dispersion. For example, the canister connection point 110 can include an adjustable control valve that can open and close (turn on and off) the flow of gas from the canister(s) in a regulated manner. In another example, depressing a ball bearing (or other mechanism) different amounts for release/delivery of different rates/pressures. In some embodiments, the device 100, or a component therein, can regulate the pressure and flow of dispersion internally. For example, the device 100, or a component therein, can regulate the pressure and flow of dispersion by using a specifically sized small tube, made of glass, stainless steel, or other material with a very smooth surface and strength. The inside diameter of tube which the gas will pass through where at the other end it is a prescribed pressure and flow rate because of that diameter and gas properties. In such instances, the full contents or a portion of the contents of the canister 200 can be released to be controlled by the internal design of the device 100.

In some embodiments, the dispersion mechanism can be triggered to release from the canister 200 and/or the volume and pressurization within the canisters 200 themselves can be configured to provide the released fluid at a predetermined rate, pressure, volume, etc. For example, the dispersion mechanism can activate a valve, depress a ball bearing (or other valve structure), etc. at a release point of a canister 200, releasing a portion of or an entirety of the fluid stored therein at a rate based on the pressurization within the canister 200. Similarly, the rate of flow can be controlled by the dispersion mechanism itself, for example, by controlling an amount of fluid being dispersed at a given point in time.

In some embodiments, the activation/de-activation of a dispersion and rate of dispersion from the canisters 200 can be managed by a control mechanism. The control mechanism can include any combination of electro-mechanical systems mechanisms for activating a controlled a flow of fluid. For example, the control mechanism can be a button activating a valve or other dispersion mechanism. The control mechanism can be activated/de-activated using a combination of mechanisms. For example, the activation/de-activation can be controlled from a mechanism on the housing 102, such as a dial, button, switch, etc., can be utilized to manually control of the delivery properties (e.g., flow rate, pressure, etc.) of the media from within the canisters 200.

In some embodiments, an operator can activate the control mechanism to release media up to a predetermined pressure or predetermined flow rate automatically controlled/set by the dispersion mechanism, for example, as regulated by a pressure regulator. The control mechanism can be used to create a one press activation to eliminate the need to use a button to turn flow on and off repeatedly and just use the dispersion mechanism and pressure regulators to constantly automatically adjust the flow (e.g., via a valve) to achieve the desired internal pressure, without the operator having to get involved. In another embodiment, the amount of pressure could be manually regulated by an operator. The desired internal pressure or flow rate maybe be something that can be designed to be both adjustable by the operator or not adjustable.

In some embodiments, the canisters 200 can be self-regulated and different canisters 200 can be selected for different tasks. For example, different canisters 200 with different properties (e.g., media type, volume, pressurization, etc.) can be selected and utilized without requiring the user to manually adjust the properties (e.g., flow rate). In some embodiments, self-regulated canisters 200 can have one-time activations (e.g., via the control mechanism) to release the media at the predetermined volume, pressure, flow rate, etc. or a combination thereof.

In some embodiments, an elongated body 104 can extend longitudinally from the distal end of the housing 102. The elongated body 104 can be substantially solid or hollow and have a proximal end 106 and a distal end 108. The proximal end 106 can be coupled to and/or within the housing 102 using any combination of coupling mechanisms. In some embodiments, the elongated body 104 can include an inner cavity 202 extending from the proximal end 106 to the distal end 108 to enable transmission of media from the canister connection point 110 out the distal end 108 (or other output location on the device 100). The canister connection point 110 can be coupled to the elongated body 104 such that a fluid communication pathway is established from the canister 200 through the elongated body 104 and out the distal end 108. As would be appreciated by one skilled in the art, the elongated body 104 can house and/or be coupled to a variety of other tools or components, for example, a cutting tool.

In some embodiments, the elongated body 104 can be configured for passing extravascularly through an entry incision to a vessel harvesting site and configured to introduce media from the canister 200 coupled to the canister connection point 110 and in fluid communication with the elongated body 104 to the incision site. To aid in navigating the elongated body 104 to a site of harvesting, the elongated body 104 may be sufficiently rigid axially along its length.

To provide the elongated body 104 with such characteristic, in an embodiment, the elongated body 104 may be made from a biocompatible material, such as, plastic material, elastomeric material, metallic material, shape memory material, composite material or any other materials that has the desired characteristics. To the extent desired, the elongated body 104 may be provided with some flexibility to move radially or laterally from side to side depending on the application.

In some embodiments, the elongated body 104 of the device 100 may be solid. In other embodiments, the device 100 may include one or more lumen with lumen that accommodate advancing instruments, wires, or materials therethrough. The elongated body 104 can also include lumens for transporting media from the canisters 200 through and out of the device 100, for example, out the tip 120. In some embodiments, the device 100 may include a conduit through which wires or cabling may be advanced for powering and/or communicating with electrical components within the device 100. Similarly, the device 100 can include a conduit for transmission of media from the canister 200 coupled to the canister connection point 110 to a desired destination outside the distal end 108 or other output on the device 100. The lumen and/or conduit for transmission of the media can be shared with the other components or can be an isolated separate conduit exiting out the tip 120 of the device 100. In some embodiments, the media can be transmitted using spaces that already exist within the elongated body 104 to seal off the media and allow it to pass down a length of the elongated body 104 (e.g., between the electrode layers).

In some embodiments, elongated body 104 can terminate at the dissection tip 120 or can have a dissection tip 120 coupled to the distal end 108 of the elongated body 104. In some embodiments, the dissection tip 120 may include a generally tapered section which terminates in a generally blunt end for atraumatic separation of a vessel segment, being harvested from surrounding tissue, while minimizing or preventing tearing or puncturing of nearby vessels or tissue as the device 100 is navigated along a vessel segment. Although illustrated as being blunt, it should of course be understood that, to the extent desired, the end of the dissection tip 120 may be made relatively pointed to enhance advancement of the distal end of the device 100. Similarly, the tapered section may be configured differently structurally, so as to enhance the operability of the device 100. In some embodiments, the tip 120 can include at least one opening for enabling the media to disperse therethrough.

In some embodiments, to reduce likelihood of trauma during a dissection process, in some embodiments, the dissection tip 120 may be radially pliable, flexible or deformable so that the dissection tip may deflect slightly under exertion of force applied to the dissection tip 120. In some embodiments, the dissection tip 120 is radially compressible so that the walls of the dissection tip 120 can deform under exertion of force normal to the tip surface. To that end, the dissection tip 120 may be formed from thin wall plastic material to enable the dissection tip to flex under load. Suitable materials include, but are not limited to, polycarbonate, polyethylene terephthalate glycol-modified (PETG), polyethylene terephthalate (PET) and other materials that provide enough optical clarity while allowing the dissection tip 120 to flex under load. At the same time, the dissection tip 120 may be provided with sufficient column strength in the axial or longitudinal direction to allow dissection of the vessel from the surrounding connective tissue.

Other characteristics of the dissection tip 120 are contemplated, such as having variable strengths: (1) in an axial direction versus a longitudinal direction, wherein the axial strength is greater than the longitudinal strength; (2) in a longitudinal direction versus an axial direction, wherein the longitudinal strength is greater than the axial strength; or (3) the axial direction versus a longitudinal direction, wherein the axial strength is approximate the longitudinal strength. It is also possible that the dissection tip 120 may include two or more materials, wherein at least one material can have different material properties, such as elasticity, hardness, tensile strength.

In operation, the EVH device 100 of the present invention can be used to provide a gas/fluid media independent from a remote tank(s) and/or using external tubing during a procedure as provided in conventional systems. For example, the canister 200 system of EVH device 100 of the present invention can be used to provide $CO_2$ from canisters 200 coupled to the device 100 for use during a vessel harvesting procedure. When using the EVH device 100, the user can first make an incision 'I' at a desired location as normal. The user can also implement a tip search or cut down method if desirable.

In some embodiments, the user can utilize sealing device 300, such as a gas pad, to create a seal between the patient and the EVH device 100. For example, a user can use a gas seal pad such as the gas seal pad discussed in U.S. patent application Ser. No. 16/225,049, incorporated herein by reference. With the elongated body 104 and/or gas pad in place and insufflation is ready to begin, the user can engage the release of the media from the canister(s). For example, the media can be released from the canisters 200 coupled to the canister connection point 110 under pressure by activating a control mechanism (e.g., a button) on the housing 102. At this point the contents of the canister(s) 200 can be triggered to release the stored media (e.g., $CO_2$) through the device 100, via a dispersion mechanism and through the elongated body 104, into the patient. A mechanism internal to the EVH device 100 can be used to control the pressure and flow rate (e.g., pressure sensors, regulator, etc.) of the media delivered from the canister 200. If the user would like to remove the EVH device 100 or otherwise stop flow/pressure, the user can disengage the release or pressure through the same control mechanism on the handle 102.

Figure 3A:
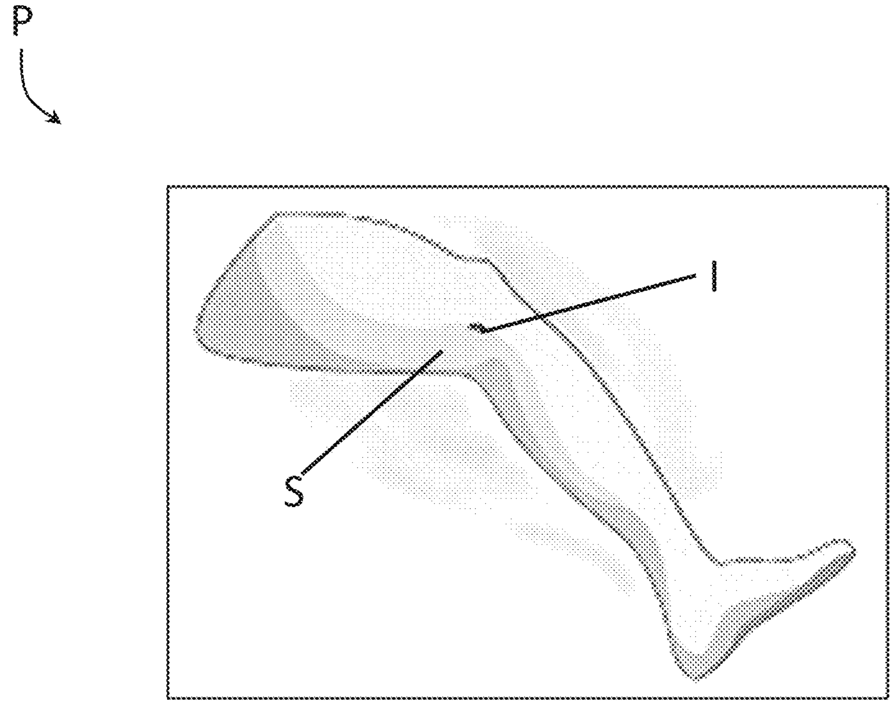
FIGS. 3A, 3B, 3C, 3D, and 3E are diagrams illustrating steps for another method of using the sealing device of FIGS. 1 and 2A-2C in accordance with various embodiments.

Referring to FIGS. 3A-3E, an exemplary method for using the EVH device 100 is provided. Although the example provided in FIGS. 3A-3E are applied to a specific procedure on a specific body part, the present invention is not intended to be limited to this procedure, body part, media, etc. and is merely provided for illustration purposes. As shown in FIG. 3A, the user can place an initial incision I in the skin S of a patient leg P, using any system or method known in the art. In an optional step, an adhesive of a sealing device 300 can then be placed onto the skin S to form a gas seal between the patient and the device 100, wherein the port 103 is positioned over the incision I, prior to insertion of the device into incision I.

Figure 3B:
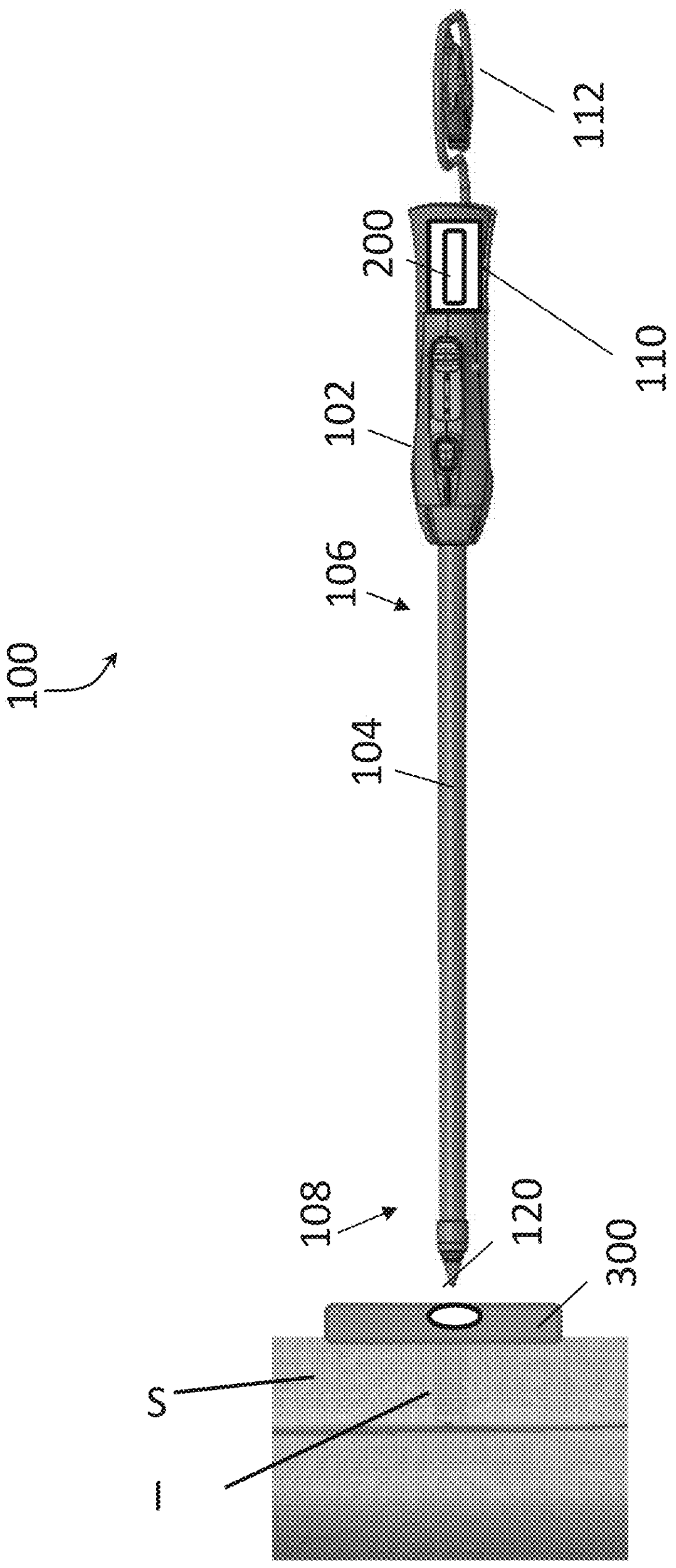
Figure 3C:
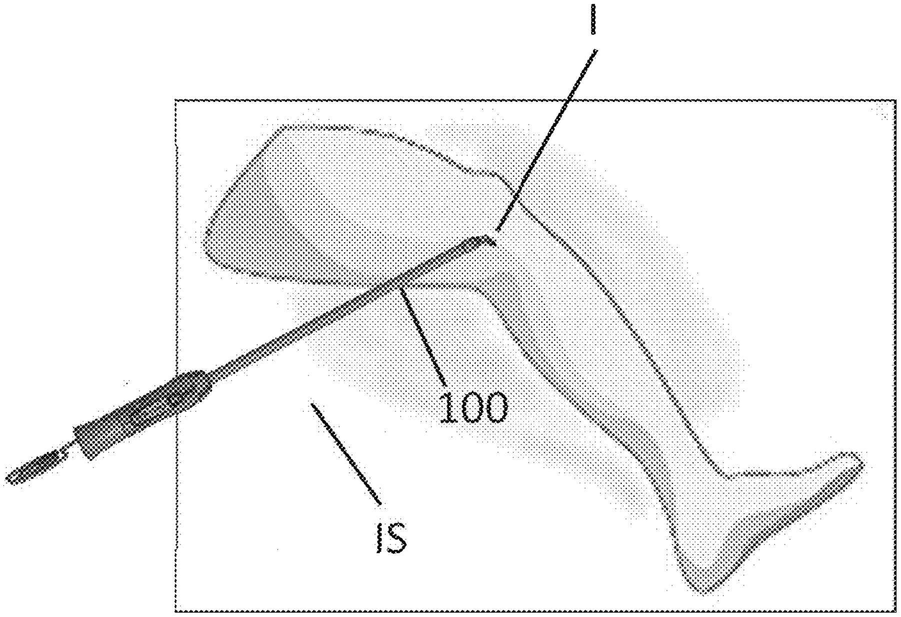

Referring now to FIG. 3B, in some embodiments, such as, for example, a tip-search technique procedure, the user can insert a tip 120 of a device 100 through a port 302 of a sealing device 300 to form a gas seal between the device 100 and the sealing device 300. As shown in FIG. 3C, the user can advance the tip 120 and at least a portion of the elongated body 104 of the surgical device 100 into the patient via the incision I until the desired surgical site is reached (e.g., a targeted vessel for harvesting).

Figure 3D:
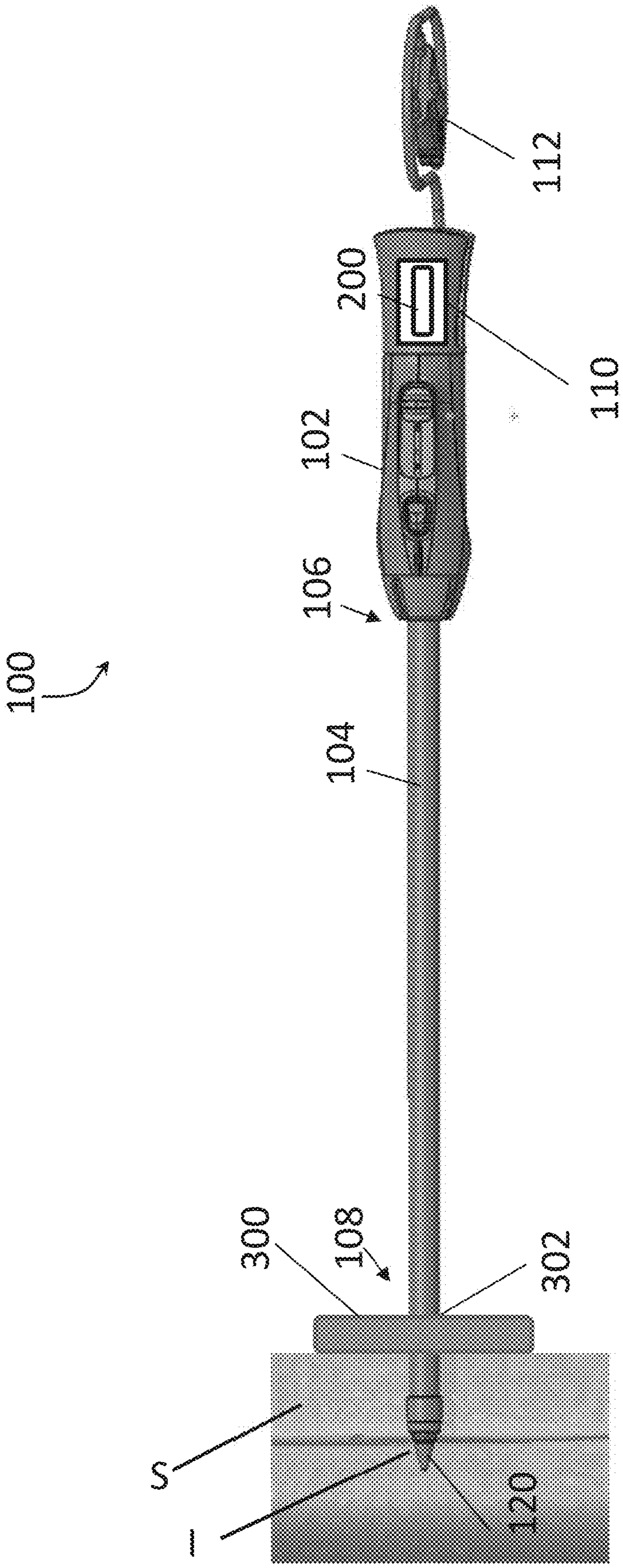

Referring to FIG. 3D, once the gas seal is formed between the device 100 and the incision site, insufflation media from the one or more canisters 200 can be communicated into the surgical site. Specifically, when insufflation is ready to begin, the user can engage the release of pressurized media from the canister 200 through an activation of a mechanism/button on the housing 102. At this point the internal canister(s) 200 can be opened/activated to release the stored media, such as $CO_2$, into the patient. A mechanism internal to device 100 can be used to control the pressure and flow rate delivered from the canister 200. The gas from the canister(s) 200 can be insufflated through a fluid communication path extending through the device 100 and out the tip 120 or any point beyond the seal with the body. With the device 100 placed through the port toward the surgical site, a number of tasks can be performed. The tasks include, but are not limited to, accessing a target anatomical structure within the surgical site (e.g., via tip 120 of the instrument 100), communicating a fluid flow from the one or more canister(s) 200 into the surgical site, harvesting/removing material from the surgical site, incising at the surgical site, or a combination thereof.

If the user would like to remove the device 100 or otherwise stop flow/pressure of the media, the user can disengage the release or pressure through the same mechanism/button on the housing 102 as was used to activate the release of the media from the canister(s) 200. In some embodiments, if additional or different media is needed, the canister 200 can be replaced with a new or different canister 200. For example, the user can be decoupled and removed the canister 200 from the canister connection point 110 and a new canister 200 can be coupled to the canister connection point 110 for use. In some embodiments, an empty canister can be refilled or it can be unplugged and swapped out for a full canister. When using replaceable canisters 200, a quick reload mechanism, such as a magazine setup can be used to quickly reload the media.

Figure 3E:
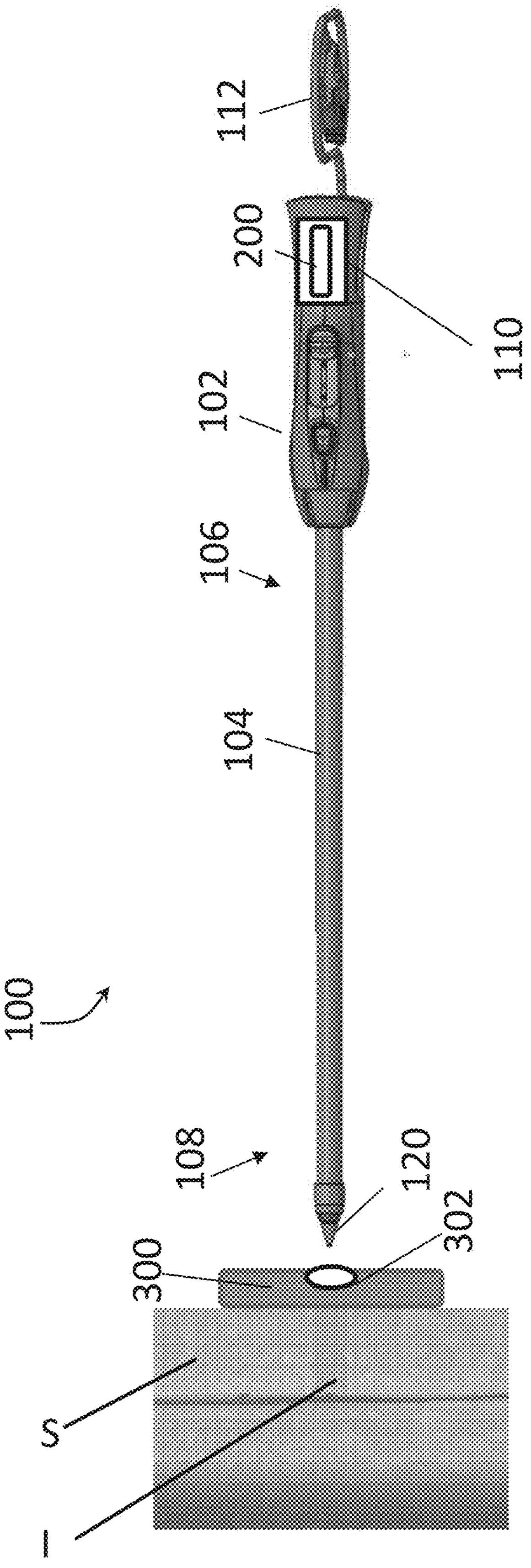

With the device 100 in place and insufflating performed, as shown in FIG. 3D, the surgical device 100 can be used to perform a surgical procedure such as harvesting a vessel in an EVH procedure. As shown in FIG. 3E, the device 100 can be withdrawn from the port 103 and the sealing device 300 can be removed from the patient's skin S. Although described in a particular order herein, it will be apparent in view of this disclosure that the steps of placing an incision I, cutting down, placing the device 100, insufflating the surgical site, inserting the device 100, and withdrawing the device 100 can be performed in any order as appropriate for a particular medical procedure.

While the present disclosure has been described with reference to certain embodiments thereof, it should be understood by those skilled in the art that various changes may be made and equivalents may be substituted without departing from the true spirit and scope of the disclosure. In addition, many modifications may be made to adapt to a particular situation, indication, material and composition of matter, process step or steps, without departing from the spirit and scope of the present disclosure. All such modifications are intended to be within the scope of the claims appended hereto.

As utilized herein, the terms "comprises" and "comprising" are intended to be construed as being inclusive, not exclusive. As utilized herein, the terms "exemplary", "example", and "illustrative", are intended to mean "serving as an example, instance, or illustration" and should not be construed as indicating, or not indicating, a preferred or advantageous configuration relative to other configurations. As utilized herein, the terms "about", "generally", and "approximately" are intended to cover variations that may existing in the upper and lower limits of the ranges of subjective or objective values, such as variations in properties, parameters, sizes, and dimensions. In one non-limiting example, the terms "about", "generally", and "approximately" mean at, or plus 10 percent or less, or minus 10 percent or less. In one non-limiting example, the terms "about", "generally", and "approximately" mean sufficiently close to be deemed by one of skill in the art in the relevant field to be included. As utilized herein, the term "substantially" refers to the complete or nearly complete extend or degree of an action, characteristic, property, state, structure, item, or result, as would be appreciated by one of skill in the art. For example, an object that is "substantially" circular would mean that the object is either completely a circle to mathematically determinable limits, or nearly a circle as would be recognized or understood by one of skill in the art. The exact allowable degree of deviation from absolute completeness may in some instances depend on the specific context. However, in general, the nearness of completion will be so as to have the same overall result as if absolute and total completion were achieved or obtained. The use of "substantially" is equally applicable when utilized in a negative connotation to refer to the complete or near complete lack of an action, characteristic, property, state, structure, item, or result, as would be appreciated by one of skill in the art.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A powered endoscopic vessel harvesting (EVH) device, comprising:

a body including a cavity into which at least a first canister of a media is inserted;

a tapered tip disposed at a distal end of the body and in fluid communication with the first canister via a conduit in the body, the tapered tip having a design to facilitate advancement of the body to a site of interest and through which the media from the first canister can be directed to the site of interest through the conduit, wherein wiring for powering and/or communicating with electrical components within the EVH device extends through the conduit such that the wiring and the media share said conduit;

a control mechanism positioned on the body and including a coupling mechanism extending within the cavity such that, upon initial engagement of the first canister with the coupling mechanism: (a) the media can be released from the first canister into the conduit in the body and towards the tapered tip upon activation of the control mechanism; and (b) any remaining media can be contained within the first canister upon deactivation of the control mechanism; and a dispersion mechanism coupled to the body and being variable for controlled release of a flow rate of the media out of the tapered tip.

2. The powered endoscopic vessel harvesting (EVH) device of claim 1, wherein the conduit is an insufflation conduit.

3. The powered endoscopic vessel harvesting (EVH) device of claim 1, wherein the conduit is an irrigation conduit.

4. The powered endoscopic vessel harvesting (EVH) device of claim 1, wherein the first canister is a pressurized canister.

5. The powered endoscopic vessel harvesting (EVH) device of claim 1, wherein the first canister is pressurized from approximately 800 psi to 1200 psi.

6. The powered endoscopic vessel harvesting (EVH) device of claim 1, wherein the media in the first canister is an insufflation fluid or an irrigation fluid.

7. The powered endoscopic vessel harvesting (EVH) device of claim 1, wherein the media in the first canister is CO2.

8. The powered endoscopic vessel harvesting (EVH) device of claim 1, wherein the tapered tip is optically clear.

9. The powered endoscopic vessel harvesting (EVH) device of claim 1, further comprising a cutting tool designed to harvest a sample.

10. The powered endoscopic vessel harvesting (EVH) device of claim 1, wherein a pressure of the media can be automatically adjusted by the dispersion mechanism to be released to the site of interest.

11. A surgical method, comprising:

providing an endoscopic vessel harvesting (EVH) device including:

a body including a cavity at a proximal end portion of the body and into which at least a first canister of a media is inserted to engage a coupling mechanism of the body;

a tapered tip disposed at a distal end of the body and in fluid communication with the first canister via a conduit in the body;

wiring for powering and/or communicating with electrical components within the EVH device, wherein the wiring extends through the conduit in the body such that the wiring and the media share said conduit;

a control mechanism for controlled release of the media out of the first canister into the conduit in the body; and a dispersion mechanism coupled to the body and being variable for controlled release of a flow rate of the media out of the body through the tapered tip;

activating, after the first canister has been engaged with the coupling mechanism, the control mechanism to controllably release the media from the first canister into the conduit in the body of the EVH device;

directing the tapered tip to a site of interest; and engaging the dispersion mechanism to release the media out of the body through the tapered tip to the site of interest.

12. The surgical method of claim 11, wherein the engaging step includes insufflating a body part of a patient.

13. The surgical method of claim 11, wherein the engaging step includes irrigating a body part of a patient.

14. The surgical method of claim 11, further comprising placing a sealing device at an incision site on a body part of a patient to create a gas seal.

15. The surgical method of claim 14, wherein the step of placing further comprises adhering, by an adhesive disposed over at least a portion of a surface of the sealing device, the sealing device to the incision site.

16. The surgical method of claim 15, further comprising advancing the tip of the EVH device to a target anatomical structure.

17. The surgical method of claim 11, wherein the tapered tip is optically clear.

18. The surgical method of claim 11, wherein the EVH device further includes a cutting tool designed to harvest a sample.

19. The surgical method of claim 11, wherein a pressure of the media can be automatically adjusted by the dispersion mechanism to be released to the site of interest.

20. A surgical method, comprising:

engaging a canister of a media with a coupling mechanism positioned adjacent one end of an endoscopic vessel harvesting (EVH) device;

adjusting a control mechanism of the EVH device between: (a) an activation position which releasably controls a flow of the media from the canister towards an opposing end of the EVH device through a conduit in the EVH device; and (b) a deactivation position which retains any remaining media within the canister; and variably opening a dispersion mechanism situated at the opposing end of the EVH device to adjustably control delivery of the media from within the EVH device to a site of interest, wherein wiring for powering and/or communicating with electrical components within the EVH device extends through the conduit in the EVH device such that the wiring and the media share said conduit.

* * * * *